(12) United States Patent
Hellyer et al.

(10) Patent No.: US 6,770,752 B2
(45) Date of Patent: Aug. 3, 2004

(54) SEQUENCES FOR DETECTION OF HIV-1

(75) Inventors: Tobin J. Hellyer, Owings Mills, MD (US); Qimin You, Lake Zurich, IL (US); James M. Harris, Columbia, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/757,207

(22) Filed: Jan. 9, 2001

(65) Prior Publication Data

US 2002/0150880 A1 Oct. 17, 2002

(51) Int. Cl.$^7$ .............................................. C07H 21/04
(52) U.S. Cl. ......................... 536/24.33; 435/5; 435/6; 435/91.2; 536/23.1; 536/23.72; 536/24.3
(58) Field of Search ............................... 435/5, 6, 91.2; 536/23.1, 23.72, 24.3, 24.33; 935/77, 78

(56) References Cited

U.S. PATENT DOCUMENTS

| | | | |
|---|---|---|---|
| 5,008,182 A | 4/1991 | Sninsky et al. ................. | 435/5 |
| 5,176,995 A | 1/1993 | Sninsky et al. ................. | 435/6 |
| 5,386,022 A | 1/1995 | Sninsky et al. .......... | 536/24.32 |
| 5,403,707 A | 4/1995 | Atwood et al. ................. | 435/5 |
| 5,569,582 A | 10/1996 | Tavernarakis et al. ......... | 435/5 |
| 5,594,123 A | 1/1997 | Sninsky et al. .......... | 536/24.32 |
| 5,599,662 A | 2/1997 | Respess .......................... | 435/5 |
| 5,674,680 A | 10/1997 | Saksela et al. ................. | 435/5 |
| 5,688,637 A | 11/1997 | Moncany et al. .............. | 435/6 |
| 5,712,385 A | 1/1998 | McDonough et al. .... | 536/24.32 |
| 5,856,088 A | * 1/1999 | McDonough et al. .......... | 435/5 |
| 5,928,869 A | * 7/1999 | Nadeau et al. ................. | 435/6 |
| 5,962,665 A | * 10/1999 | Kroeger et al. ............ | 536/23.1 |

FOREIGN PATENT DOCUMENTS

| | | |
|---|---|---|
| EP | 0 617 132 A2 | 9/1994 |
| EP | 0 731 175 A2 | 9/1996 |
| EP | 0 854 197 A2 | 7/1998 |
| EP | 0 887 427 A2 | 12/1998 |
| WO | 9603528 A2 | 2/1996 |

OTHER PUBLICATIONS

A. Holguin et al., Comparison of Three Different Commercial Methods for Measuring Plasma Viraemia in Patients Infected with Non–B HIV–1 Subtypes, Eur J Clin Microbial Infect Dis (1999) 18:256–259; B. Parekh, Impact of HIV Type 1 Subtype Variation on Viral RNA Quantitation, Aids Research and Human Retroviruses, vol. 15, No. 2, 1999, 133–142; M.P. DeBaar et al., Design and Evaluation of a Human Immunodeficiency Virus Type 1 RNA Assay Using Nucleic Acid.

Sequence–Based Amplification Technology Able to Quantify Both Group M and O Viruses by Using the Long Terminal Repeat as Target, J of Clin Microbiology, Jun. 1999, 1813–1818; Z. Debyser, Failure to Quantify Viral Load with Two of the Three Commerical Methods in a Pregnant Woman Harboring an HIV Type 1 Subtype G Strain, Aids Research and Human Retroviruses, vol. 14, No. 5, 1998.

M. Segondy, et al., Evaluation of the Nuclisens HIV–1 QT Assay for Quantitation of Human Immunodeficiency Virus Type 1 RNA Levels in Plasma, J of Clin Microbiology, Nov. 1998, 3372–3374; E. Gobbers, et al., Reactivity and Amplification Efficiency of the NASBA HIV–1 RNA Amplification System with Regard to Different HIV–1 Subtypes, J of Virological Methods, 66, 1997, 293–301; C.M. Nycz, et al., Quantitative Reverse Transcription Strand Displacement Amplification: Quantitation of Nucleic Acids.

Using an Isothermal Amplification Technique, Analytical Biochemistry, 259–226–234, 1998; M. Mehrpouyan, A Rapid and Sensitive Method for Non–isotopic Quantitation of HIV–1 RNA Using Thermophilic SDA and Flow Cytometry, Molecular and Cellular Probes, 1997, 11, 337–347.

* cited by examiner

*Primary Examiner*—Ulrike Winkler
(74) *Attorney, Agent, or Firm*—Allan M. Kiang

(57) ABSTRACT

Primers and probes derived from the HIV-1 pol gene which facilitate detection and/or quantification of all presently known genotypes of HIV-1 (A-I and O). Disclosed sequences may be used in a variety of amplification and non-amplification formats for detection of HIV nucleic acids.

3 Claims, 1 Drawing Sheet

SEQUENCES FOR DETECTION OF HIV-1

FIELD OF THE INVENTION

The present invention relates to materials and methods for detection of HIV nucleic acids, in particular to probes and primers for detection of HIV in hybridization and amplification assays.

BACKGROUND OF THE INVENTION

The genome of the Human Immunodeficiency Virus (HIV) is highly heterogeneous and exhibits a mutation rate on the order of $10^{-4}$ per base per generation. Combined with the rapid rate of viral propagation in infected individuals, this presents particular challenges for diagnostic nucleic acid amplification techniques which typically amplify a single conserved sequence within a target organism. Although a great deal of research activity has been directed to detecting HIV-1 in hybridization and amplification assays, such molecular assays have so far been limited by their inability to detect all genotypes with equal efficiency. Although a signal amplification system for the detection of HIV-1 type O has been reported, none of the currently available diagnostic nucleic acid amplification methods are able to detect this genotype of the virus.

SUMMARY OF THE INVENTION

The present invention provides primers and probes derived from the HIV-1 pol gene which facilitate detection and/or quantification of all presently known genotypes of HIV-1 (A-I and O). A single amplification primer pair according to the invention efficiently amplifies all known genotypes of HIV-1, which may then be detected in a single detection step using the detector probes and primers of the invention.

DETAILED DESCRIPTION OF THE INVENTION

Figure 1:
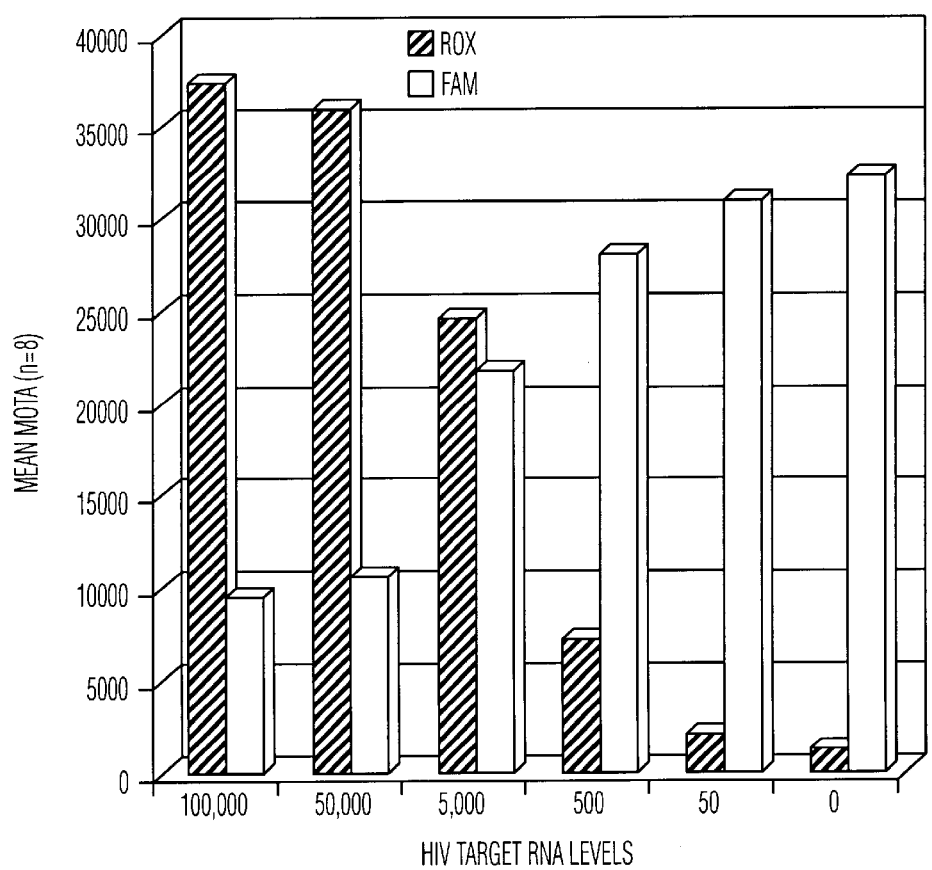
FIG. 1 shows the titration of internal control fluorescent signal (FAM) with increasing levels of native HIV target (ROX).

The primers, hybridization probes and detector probes of the present invention are complementary to regions of the HIV-1 polymerase (pol) gene. Initially, design of the disclosed primers and probes was based on conserved regions in an alignment of fifty-eight HIV-1 pol sequences. Additional data was subsequently added to the alignment to provide a database with a total of 115 pol sequences. One goal was to develop probes and primers which, in spite of the heterogeneity of the pol sequence, provided amplification, detection and/or quantitation of all presently known HIV-1 genotypes with essentially equal efficiency in amplification reactions. In some cases this was accomplished by overlapping the hybridization site of the 5' ends of certain of the detector probes with the hybridization site of the 3' end an amplification primer. This approach took advantage of sequence conservation in the SDA primer region and avoided much of the sequence heterogeneity evident in the intervening region between the two SDA primers. This technique also allowed use of a smaller target sequence, thereby improving amplification efficiency.

As used herein, an amplification primer is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in SDA include a restriction endonuclease recognition site 5' to the target binding sequence (U.S. Pat. Nos. 5,270,184 and 5,455,166). NASBA, 3SR and transcription based amplification primers require an RNA polymerase promoter linked to the target binding sequence of the primer. Linking such specialized sequences to a target binding sequence for use in a selected amplification reaction is routine in the art. In contrast, amplification methods such as PCR, which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantitation of HIV-1 may be used either as hybridization probes or as target binding sequences in primers for detection or amplification, optionally linked to a specialized sequence required by the selected amplification reaction or to facilitate detection.

Based on the alignment of multiple HIV-1 pol gene sequences, the following amplification primers were designed for testing in SDA reactions. Target binding sequences are underlined. The remaining 5' portion of the sequence comprises the restriction endonuclease recognition site (RERS) that is required for the SDA reaction to proceed and a generic non-target-specific tail sequence. It will be readily apparent that the target binding sequences may be used alone to amplify the target in reactions which do not require specialized sequences or structures (e.g., PCR) and that different specialized sequences required by amplification reactions other than SDA may be substituted for the RERS-containing sequence shown below (e.g., an RNA polymerase promoter). "R" and "L" in the primer name indicates "right" and "left" primers, respectively, when the oligonucleotides are used in amplification reactions:

| AMPLIFICATION PRIMERS | | |
|---|---|---|
| QAL48 | CGATTCCGCTCCAGACTTCTCGGGTAGATACAGGAGCAGAT | SEQ ID NO:1 |
| QAL46 | CGATTCCGCTCCAGACTTCTCGGGAGATACAGGAGCAGAT | SEQ ID NO:2 |
| QAR48 | ACCGCATCGAATGCATGTCTCGGGCTATCATTTTTGGTTTCC | SEQ ID NO:3 |
| QAR44 | ACCGCATCGAATGCATGTCTCGGGTATCATTTTTGGTTTCC | SEQ ID NO:4 |
| AL46 | CGATTCCGCTCCAGACTTCTCGGGCAGTACAAATGGCAGT | SEQ ID NO:5 |
| AL48 | CGATTCCGCTCCAGACTTCTCGGGGCAGTACAAATGGCAG | SEQ ID NO:6 |
| AL50 | CGATTCCGCTCCAGACTTCTCGGGGCAGTACAAATGGCAGT | SEQ ID NO:7 |
| AR44 | ACCGCATCGAATGACTGTCTCGGGTGTACCCCCCAATC | SEQ ID NO:8 |
| AR44B | ACCGCATCGAATGACTGTCTCGGGCTGTACCCCCCAAT | SEQ ID NO:9 |
| AR48 | ACCGCATCGAATGACTGTCTCGGGTGTACCCCCCAATCC | SEQ ID NO:10 |

In addition, the following detector primers were designed for real-time detection of amplification products produced using the amplification primers. The structure and use of such detector primers is described, for example, in U.S. Pat. Nos. 5,547,861 and 5,928,869. The target binding sequences are underlined. The remaining portion of the sequence forms a hairpin structure which is typically labeled to facilitate detection of amplification products as is known in the art. It will be readily apparent that the target sequence may be used alone for direct detection by hybridization (typically linked to a detectable label) and that other directly and indirectly detectable sequences and labels may be substituted for the hairpin as is known in the art. See, for example U.S. Pat. Nos. 5,935,791; 5,846,726; 5,691,145; 5,550,025 and 5,593,867.

| DETECTOR PRIMERS | | |
|---|---|---|
| QDR66 | TAGCACCCGAGTGCTGGCAAATTCATTTCTTCTAATACTG | SEQ ID NO:11 |
| QDR64 | TAGCACCCGAGTGCTGCAAATTCATTTCTTCTAATACTGT | SEQ ID NO:12 |
| QDR56 | TAGCACCCGAGTGCTAAATTCATTTCTTCTAATACTGT | SEQ ID NO:13 |
| QOL1 | TAGCACCCGAGTGCTAGGAGCAGATGATACAGT | SEQ ID NO:14 |
| QOL2 | TAGCACCCGAGTGCTCAGGAGCAGATGATACAGT | SEQ ID NO:15 |
| QOL3 | TAGCACCCGAGTGCTACAGGAGCAGATGATACAGT | SEQ ID NO:16 |
| QOL4 | TAGCACCCGAGTGCTGAGCAGATGATACAGT | SEQ ID NO:17 |
| QOL5 | TAGCACCCGAGTGCTGGAGCAGATGATACAGT | SEQ ID NO:18 |
| DL56HPD | TAGCACCCGAGTGCTCACAATGTTAAAAGAAAAGGG | SEQ ID NO:19 |
| DL52HPD | TAGCACCCGAGTGCTACAATGTTAAAAGAAAAGGG | SEQ ID NO:20 |
| DL50HPD | TAGCACCCGAGTGCTCAATGTTAAAAGAAAAGGG | SEQ ID NO:21 |
| DR58HPD | TAGCACCCGAGTGCTCCCCTTTTCTATTAAAATTGTG | SEQ ID NO:22 |
| DR54HPD | TAGCACCCGAGTGCTCCCTTTTCTATTAAAATTGTG | SEQ ID NO:23 |
| DR52HPD | TAGCACCCGAGTGCTCCCCTTTTCTATTAAAATTG | SEQ ID NO:24 |
| DR48HPD | TAGCACCCGAGTGCTCCCTTTTCTATTAAAATTG | SEQ ID NO:25 |
| Pol2DR58 | TAGCACCCGAGTGCTCCCCTTTTCTTTTAAAATTGTG | SEQ ID NO:26 |
| DN2 | TAGCACCCGAGTGCTCCCAATCCCCCCTTTTCTGTTAAAAT | SEQ ID NO:27 |
| DN3 | TAGCACCCGAGTGCTCCCCAATCCCCCCTTTTCTGTTAAAAT | SEQ ID NO:28 |
| DN4 | TAGCACCCGAGTGCTCCAATCCCCCCTTTTCTGTTAAAAT | SEQ ID NO:29 |

-continued

| DETECTOR PRIMERS | | |
|---|---|---|
| DN5 | TAGCACCCGAGTGCT<u>CAATCCCCCCTTTTCTGTTAAAAT</u> | SEQ ID NO:30 |
| DN5.1 | TAGCACCCGAGTGCT<u>CAATCCCCCCTTTTCTTTTAAAAT</u> | SEQ ID NO:31 |
| OL62 | TAGCACCCGAGTGCT<u>CCCAATCCCCCCTTTTCTTTT</u> | SEQ ID NO:32 |
| OL64 | TAGCACCCGAGTGCT<u>CCCAATCCCCCCTTTTCTTTTA</u> | SEQ ID NO:33 |

SEQ ID NOs:11–13 and 19–26 are conventional non-overlapping detector primers which contain a hairpin as described in U.S. Pat. No. 5,928,869. SEQ ID NOs:14–18 and 27–33 also contain the hairpin but the 5' end of the target binding sequences overlap with the 3' end of the target binding sequences of the upstream amplification primers.

Bumper primers used in SDA (BR and BL) were also designed. The entire sequence of these oligonucleotides consists of target binding sequence:

| BUMPER PRIMERS/DETECTOR PROBES | | |
|---|---|---|
| QBL44 | CTAAAGGAAGCTCTAT | SEQ ID NO:34 |
| QBR42 | AACCTCCAATTCCC | SEQ ID NO:35 |
| BL54 | GAATCTATGAATAAAGAATTAAA | SEQ ID NO:36 |
| BR54 | TGCTATTATGTCTACTATTCT | SEQ ID NO:37 |

The sequences set forth above were selected to minimize the effects of heterogeneity in the targeted region of the pol gene. Mismatches were confined to the middle or the 5' end of the sequences to permit efficient 3' extension upon hybridization to the target sequence. Only three of the 117 HIV-1 strains analyzed exhibit more than one mismatch with amplification primers SEQ ID NO:5 and SEQ ID NO:9 or with detector SEQ ID NO:26. Detector SEQ ID NO:27–30 contain a deliberate mismatch eight bases from the 3' end to minimize target-specific variations in priming efficiency caused by heterogeneity in the target region.

Because the target binding sequence confers target specificity on the primer or probe, it should be understood that the target binding sequences exemplified above for use as particular components of a specific amplification reaction may also be used in a variety of other ways for detection of HIV. For example, the target binding sequences of SEQ ID NOs:1–37 may alternatively be used as hybridization probes for direct detection of HIV-1, either without prior amplification or as a post-amplification assay. Such hybridization methods are well known in the art and typically employ a detectable label associated with or linked to the target binding sequence to facilitate detection of hybridization. Further, essentially all of the target binding sequences set forth above may be used as amplification primers in amplification reactions which do not require additional specialized sequences (such as PCR) or appended to the appropriate specialized sequences for use in 3SR, NASBA, transcription-based or any other primer extension amplification reactions. For detection of amplification products, amplification primers comprising the target binding sequences disclosed herein may be labeled as is known in the art, or labeled detector primers comprising the disclosed target binding sequences may be used in conjunction with the amplification primers as described in U.S. Pat. Nos. 5,547,861 and 5,928,869 for real-time homogeneous detection of amplification. Such detector primers typically comprise a directly or indirectly detectable sequence which does not initially hybridize to the target but which facilitates detection of the detector primer once it has hybridized to the target and been extended. For example, such detectable sequences may be sequences which form a secondary structure, sequences which contain a restriction site, or linear sequences which are detected by hybridization of their complements to a labeled oligonucleotide (sometimes referred to as a reporter probe) as is known in the art. Alternatively, the amplification products may be detected post-amplification by hybridization of a probe selected from any of the target binding sequences disclosed herein which fall between a selected set of amplification primers.

It is to be understood that an oligonucleotide according to the invention which consists of a target binding sequence and, optionally, either a sequence required for a selected amplification reaction or a sequence required for a selected detection reaction may also include certain other sequences which serve as spacers, linkers, sequences for labeling or binding of an enzyme, etc. Such additional sequences are typically known to be necessary to obtain optimum function of the oligonucleotide in the selected reaction and are intended to be included by the term "consisting of."

EXAMPLE 1

SDA reactions were performed to determine the analytical sensitivity of the assay for the detection of HIV DNA. Amplification was carried in the presence of 0, 5, 10, 50, 100 or 250 copies of HIV target DNA. The target sequence was a fragment of the HIV-1 genome corresponding to nucleotides 4659–4910 of strain B-WEAU (GenBank accession number U21135) that was cloned into the plasmid vector pBlueScript SK+(Stratagene). SDA was performed at 52° C. using 500 nM primers (SEQ ID NO:5 and SEQ ID NO:9), 50 nM bumpers (SEQ ID NO:36 and SEQ ID NO:37), and 200 nM detector probe, SEQ ID NO:26, in buffer containing: 100 mM bicine; 30 mM potassium hydroxide; 68 mM $K_iPO_4$, pH7.6; 10.5% glycerol; 6.5% DMSO; 0.7 mM $dC_sTP$; 0.1 mM dA-, dG- and dTTP; 70 ng/µl human placental DNA; 100 ng/µl bovine serum albumin; 4 mM magnesium acetate; 6U Bst polymerase and 32U BsoBI restriction enzyme. The detector primer was labeled at the 5' terminus with a fluorescein donor molecule and internally with a dabcyl quencher moiety. The two dyes on the detector were separated by BsoBI restriction endonuclease recognition sequence and held in close juxtaposition by a hairpin structure within the tail sequence as described in U.S. Pat. Nos. 5,919,630; 5,928,869 and 5,958,700. Donor fluorescence was monitored during the course of amplification.

In the presence of target, donor fluorescence increased during the course of the reaction as the hairpin holding the donor and quencher in close proximity unfolded and the restriction site was cleaved. In contrast, in the absence of target, fluorescence remained consistently low throughout the reaction. Results were expressed in terms of area under the curve or "MOTA." A larger MOTA score indicates generation of more fluorescence and, generally, the presence of more input target. The results are shown in Table 1.

TABLE 1

| TARGETS PER REACTION | MEAN MOTA SCORE (n = 28)* |
|---|---|
| 0 | 606 |
| 5 | 14883 |
| 10 | 20565 |
| 50 | 47643 |
| 100 | 56740 |
| 150 | 61676 |

*n = 54 for negative controls

The limit of detection (LOD), defined as the input target level at which 95% of reactions would yield a positive result, was determined to be between 9 and 11 copies of target DNA depending on the MOTA score selected as a cut-off for determining a positive result. These results demonstrate that the amplification and detector primers are capable of sensitive and reproducible detection of HIV DNA.

EXAMPLE 2

A similar experiment to that described in Example 1 was performed using the SEQ ID NO:27 detector primer, the target hybridization region of which overlaps the SEQ ID NO:9 amplification primer. This probe was designed to take advantage of sequence conservation in the amplification primer binding region while maintaining the specificity afforded by detection of the internal region of the SDA amplicon that lies between the two amplification primers. Buffer conditions were the same as described above with the following modifications: 75 mM $K_iPO_4$, 14% DMSO, 5% glycerol and 27U BsoBI. The limit of detection using the overlapping probe was 61 to 86 copies of HIV target DNA depending on the MOTA score selected for determining a positive result. These results demonstrate sensitive and specific detection of HIV target DNA using an alternative probe design that offers additional flexibility in the development of SDA-based systems.

EXAMPLE 3

The SDA assay for HIV DNA was converted to a two-step reverse transcriptase (RT)-SDA format in which RNA was first copied to cDNA using an RT enzyme and then amplified in a conventional SDA reaction. One important difference between the SDA conditions described in Examples 1 and 2 and the RT-SDA described here is the absence of bumper primers. The need for bumpers apparently was precluded by the choice of an RT enzyme which possesses RNase H activity and which is therefore capable of degrading the RNA template following reverse transcription, thereby liberating a single stranded DNA target sequence in to solution. An LOD study was performed for HIV RNA using in vitro transcripts of a genotype B strain generated from the pBlueScript plasmid clone described in Example 1.

Reverse transcription was carried out in microtiter wells using 15U avian myeloblastosis virus (AMV)-RT in buffer containing: 69.3 mM bicine; 12.3 mM KOH; 20.8 mM $K_iPO_4$; 3% glycerol; 4.5% DMSO; 6 mM magnesium acetate; 2.75 mM $dC_sTP$; 0.25 mM dA-, dG- and DTTP; 100 ng/µl BSA; 1250 nM SEQ ID NO:5 and 700 nM SEQ ID NO:9. In brief, the reverse transcription reaction mixture without enzyme was incubated for 10 min at 68° C. to denature the target RNA. Eighty microliters of denatured target was then added to a microwell containing 20 µl of an RT enzyme mixture that was pre-equilibrated at 50° C. The complete RT reaction was incubated for 10 min to facilitate synthesis of cDNA and degradation of the RNA template by the RNase H activity of the RT enzyme. To initiate amplification, 40 µl of the reverse transcription reaction was transferred to a second microtiter well at 52° C. containing 60 µl of an amplification mixture comprising Bstpolymerase, BsoBI restriction enzyme, and fluorescent detector primer together with certain buffer components. The final SDA conditions were as follows: 72 mM bicine; 24 mM potassium hydroxide; 54.4 mM $K_iPO_4$; 4% glycerol; 11% DMSO; 0.1 mM dA-, dG- and dTTP; 1.1 mM $dC_sTP$; 700 ng/µl hpDNA; 100 ng/µl BSA; 500 nM SEQ ID NO:5; 300 nM SEQ ID NO:9; 600 nM SEQ ID NO:26; 12U BsoBI and 7U Bst polymerase. The wells were sealed and incubated at 52° C. Donor fluorescence was monitored throughout the course of the reaction.

The results of this experiment are shown in Table 2.

TABLE 2

| RNA TARGETS PER REACTION | MEAN MOTA SCORE (n = 17) | % POSITIVE |
|---|---|---|
| 0 | 139 | 0 |
| 10 | 3577 | 64.7 |
| 25 | 7810 | 88.0 |
| 50 | 13410 | 100.0 |
| 75 | 23641 | 100.0 |
| 100 | 35719 | 100.0 |
| 500 | 73870 | 100.0 |

MOTA scores ≧1000 were considered positive. All reactions containing ≧50 copies of HIV target RNA were positive as were 88% containing 25 copies and 65% of those containing 10 copies. These results demonstrate the sensitivity of the disclosed amplification and detector primers for the detection of HIV-1 RNA.

EXAMPLE 4

RT-SDA was performed on purified RNA from representative isolates of nine different clades of HIV-1 (Boston Biomedica, Inc.). In order to quantify the parental stocks of viral RNA, all except the Type O nucleic acid were tested with each of two commercially available quantitative HIV tests: the Roche Amplicor HIV-1 Monitor V1.5 and the Chiron Quantiplex HIV-1 RNA 3.0 Assay. Since neither of these tests is able to amplify RNA of HIV-1 genotype O, a third non-amplified system, the Digene Hybrid Capture Assay, was used to quantify the type O nucleic acid. Viral RNAs for genotypes A–H were diluted according to the results of the Roche assay to give the equivalent of 200 copies per RT-SDA reaction. Type O RNA was diluted to the same level based on the results of the Digene test. RT-SDA was performed according to the method described in Example 3. For eight of the nine clades, all sixteen replicates were positive at 200 copies per RT-SDA reaction. For genotype F, 4/16 (25%) replicates were positive. The reason for the apparently lower sensitivity with type F is unclear but might be attributed to inaccurate qualification of the parental RNA stock of this genotype by the Roche assay. Alternatively, the discrepancy might be due to the presence in the type F sequence of a single base mismatch with the right amplification primer which is used to initiate first strand cDNA synthesis (SEQ ID NO:9). Importantly, all reactions conducted with 2000 input copies of type F RNA were psotive.

These data demonstrate that the disclosed primers and probes are capable of detecting multiple genotypes of HIV-1, including type O, with a high degree of sensitivity. Detection of type O RNA is particularly important in view of the inability to detect this lade with the majority of commercially available diagnostic nucleic acid assays.

EXAMPLE 5

In vitro transcripts generated from the plasmid clone described in Example 1 were quantified by competitive RT-SDA. In brief, RT-SDA was performed as described above with the exception that two detector primers were included in the reaction mixture, both at a concentration of 200 nM. The first primer, SEQ ID NO:26, was specific for HIV-1 and was labeled at the 5' end with dabcyl quencher moiety and internally with rhodamine (Rox). The second probe was specific for an internal control sequence and was labeled at its 5' end with fluorescein and internally with a dabcyl quencher. The internal control comprised an RNA molecule that was generated by in vitro transcription of a mutated clone of the HIV-1 pol gene. The internal control possessed the same primer binding regions as the native HIV target but differed by a series of point mutations introduced to coincide with the 3' end of the detector hybridization region. These mutations permitted discrimination of the native target and internal control by preventing hybridization and extension of the mismatched probes during amplification. The internal control was designed such that it amplified with similar efficiency to the native target and would compete during the course of the reaction for one or more rate-limiting reagents. The same amount of internal control was seeded into each test sample and into a series of calibrator reactions containing known amounts of native target. Details of the theoretical aspects of the quantitative SDA algorithm may be found elsewhere (J. G. Nadeau, et al. 1999. *Anal Biochem* 276, 177–187; C. M. Nycz, et al. 1998. *Anal Biochem* 259, 226–234). In brief, the fluorescence produced by amplification of both the native target and internal control was monitored at discreet intervals throughout the reaction. Data were processed through a series of normalization and smoothing functions to produce a fluorescent signal for both sequences. From these values, the natural log of the ratio of native target and internal control signals was calculated. The values obtained from the calibrator wells were plotted as a regression against the natural log of the input number of target molecules of RNA to produce calibration curves corresponding to each time point. An automated algorithm was then used to determine the time at which it was statistically optimal to perform quantification.

FIG. 1 shows the MOTA scores for the internal control with various copy numbers of input target sequence. MOTA scores for the internal control decreased with increasing levels of native target, demonstrating the competition between the two targets that is necessary for accurate quantification. Table 3 shows the results of quantitative competitive RT-SDA with between 50 and 100000 copies of native RNA target and 5000 copies of internal control per reaction. At all but one target level, accuracy and precision were better than ±25%, thus demonstrating the ability to quantify HIV-1 RNA using the disclosed amplification and detector primer sequences.

TABLE 3

| TARGET RNA COPIES/REACTION | | | PERCENT | |
|---|---|---|---|---|
| REVERSE TRANSCR. | SDA* | MEAN (n = 8) | ACCURACY | PRECISION |
| 0 | 0 | 16 | | 62.78 |
| 125 | 50 | 47 | −5.17 | 25.47 |
| 1250 | 500 | 537 | 7.45 | 24.19 |
| 12500 | 5000 | 8765 | 75.29 | 9.07 |
| 125000 | 50000 | 60009 | 20.02 | 5.48 |
| 250000 | 100000 | 76351 | −23.65 | 7.26 |

*Based on 100% conversion of RNA to cDNA and amplification of 40% of the reverse transcription in the SDA reaction Sequence alignment data and initial testing of the additional target binding sequences disclosed herein indicates that similar results would be obtained using these sequences in probes and primers for amplification and/or detection of all genotypes of HIV-1.

What is claimed is:

1. A method for detecting an HIV-1 target sequence comprising:

a) amplifying the target sequence using an amplification primer consisting of any one of SEQ ID NOS:5, 9 and 26 and;

b) detecting the amplified target sequence.

2. A method for detecting an HIV-1 target sequence comprising:

a) amplifying the target sequence using a first amplification primer consisting of any one of SEQ ID NOS:5 and 26 and a second amplification primer consisting of SEQ ID NO:9, and;

b) detecting the amplified target sequence.

3. An oligonucleotide selected from the group consisting of any one of SEQ ID NOS:5, 9 and 26.

* * * * *

SEQUENCE LISTING

<160> NUMBER OF SEQ ID NOS: 37

<210> SEQ ID NO 1
<211> LENGTH: 41

-continued

```
<212> TYPE: DNA
<213> ORGANISM: Human immunodeficiency virus type 1

<400> SEQUENCE: 1
cgattccgct ccagacttct cgggtagata caggagcaga t                    41

<210> SEQ ID NO 2
<211> LENGTH: 40
<212> TYPE: DNA
<213> ORGANISM: Human immunodeficiency virus type 1

<400> SEQUENCE: 2
cgattccgct ccagacttct cgggagatac aggagcagat                      40

<210> SEQ ID NO 3
<211> LENGTH: 42
<212> TYPE: DNA
<213> ORGANISM: Human immunodeficiency virus type 1

<400> SEQUENCE: 3
accgcatcga atgcatgtct cgggctatca ttttggtttt cc                   42

<210> SEQ ID NO 4
<211> LENGTH: 41
<212> TYPE: DNA
<213> ORGANISM: Human immunodeficiency virus type 1

<400> SEQUENCE: 4
accgcatcga atgcatgtct cgggtatcat ttttggtttc c                    41

<210> SEQ ID NO 5
<211> LENGTH: 40
<212> TYPE: DNA
<213> ORGANISM: Human immunodeficiency virus type 1

<400> SEQUENCE: 5
cgattccgct ccagacttct cgggcagtac aaatggcagt                      40

<210> SEQ ID NO 6
<211> LENGTH: 40
<212> TYPE: DNA
<213> ORGANISM: Human immunodeficiency virus type 1

<400> SEQUENCE: 6
cgattccgct ccagacttct cggggcagta caaatggcag                      40

<210> SEQ ID NO 7
<211> LENGTH: 41
<212> TYPE: DNA
<213> ORGANISM: Human immunodeficiency virus type 1

<400> SEQUENCE: 7
cgattccgct ccagacttct cggggcagta caaatggcag t                    41

<210> SEQ ID NO 8
<211> LENGTH: 38
<212> TYPE: DNA
<213> ORGANISM: Human immunodeficiency virus type 1

<400> SEQUENCE: 8
accgcatcga atgactgtct cgggtgtacc ccccaatc                        38

<210> SEQ ID NO 9
```

-continued

```
<211> LENGTH: 38
<212> TYPE: DNA
<213> ORGANISM: Human immunodeficiency virus type 1

<400> SEQUENCE: 9
accgcatcga atgactgtct cgggctgtac cccccaat                              38

<210> SEQ ID NO 10
<211> LENGTH: 39
<212> TYPE: DNA
<213> ORGANISM: Human immunodeficiency virus type 1

<400> SEQUENCE: 10
accgcatcga atgactgtct cgggtgtacc ccccaatcc                             39

<210> SEQ ID NO 11
<211> LENGTH: 40
<212> TYPE: DNA
<213> ORGANISM: Human immunodeficiency virus type 1

<400> SEQUENCE: 11
tagcacccga gtgctggcaa attcatttct tctaatactg                            40

<210> SEQ ID NO 12
<211> LENGTH: 40
<212> TYPE: DNA
<213> ORGANISM: Human immunodeficiency virus type 1

<400> SEQUENCE: 12
tagcacccga gtgctgcaaa ttcatttctt ctaatactgt                            40

<210> SEQ ID NO 13
<211> LENGTH: 38
<212> TYPE: DNA
<213> ORGANISM: Human immunodeficiency virus type 1

<400> SEQUENCE: 13
tagcacccga gtgctaaatt catttcttct aatactgt                              38

<210> SEQ ID NO 14
<211> LENGTH: 33
<212> TYPE: DNA
<213> ORGANISM: Human immunodeficiency virus type 1

<400> SEQUENCE: 14
tagcacccga gtgctaggag cagatgatac agt                                   33

<210> SEQ ID NO 15
<211> LENGTH: 34
<212> TYPE: DNA
<213> ORGANISM: Human immunodeficiency virus type 1

<400> SEQUENCE: 15
tagcacccga gtgctcagga gcagatgata cagt                                  34

<210> SEQ ID NO 16
<211> LENGTH: 35
<212> TYPE: DNA
<213> ORGANISM: Human immunodeficiency virus type 1

<400> SEQUENCE: 16
tagcacccga gtgctacagg agcagatgat acagt                                 35
```

```
<210> SEQ ID NO 17
<211> LENGTH: 31
<212> TYPE: DNA
<213> ORGANISM: Human immunodeficiency virus type 1

<400> SEQUENCE: 17
tagcacccga gtgctgagca gatgatacag t                              31

<210> SEQ ID NO 18
<211> LENGTH: 32
<212> TYPE: DNA
<213> ORGANISM: Human immunodeficiency virus type 1

<400> SEQUENCE: 18
tagcacccga gtgctggagc agatgataca gt                             32

<210> SEQ ID NO 19
<211> LENGTH: 36
<212> TYPE: DNA
<213> ORGANISM: Human immunodeficiency virus type 1

<400> SEQUENCE: 19
tagcacccga gtgctcacaa tgttaaaaga aaaggg                         36

<210> SEQ ID NO 20
<211> LENGTH: 35
<212> TYPE: DNA
<213> ORGANISM: Human immunodeficiency virus type 1

<400> SEQUENCE: 20
tagcacccga gtgctacaat gttaaaagaa aaggg                          35

<210> SEQ ID NO 21
<211> LENGTH: 34
<212> TYPE: DNA
<213> ORGANISM: Human immunodeficiency virus type 1

<400> SEQUENCE: 21
tagcacccga gtgctcaatg ttaaaagaaa aggg                           34

<210> SEQ ID NO 22
<211> LENGTH: 37
<212> TYPE: DNA
<213> ORGANISM: Human immunodeficiency virus type 1

<400> SEQUENCE: 22
tagcacccga gtgctcccct tttctattaa aattgtg                        37

<210> SEQ ID NO 23
<211> LENGTH: 36
<212> TYPE: DNA
<213> ORGANISM: Human immunodeficiency virus type 1

<400> SEQUENCE: 23
tagcacccga gtgctccctt ttctattaaa attgtg                         36

<210> SEQ ID NO 24
<211> LENGTH: 35
<212> TYPE: DNA
<213> ORGANISM: Human immunodeficiency virus type 1

<400> SEQUENCE: 24
tagcacccga gtgctcccct tttctattaa aattg                          35
```

```
<210> SEQ ID NO 25
<211> LENGTH: 34
<212> TYPE: DNA
<213> ORGANISM: Human immunodeficiency virus type 1

<400> SEQUENCE: 25
tagcacccga gtgctccctt ttctattaaa attg                          34

<210> SEQ ID NO 26
<211> LENGTH: 37
<212> TYPE: DNA
<213> ORGANISM: Human immunodeficiency virus type 1

<400> SEQUENCE: 26
tagcacccga gtgctcccct tttcttttaa aattgtg                       37

<210> SEQ ID NO 27
<211> LENGTH: 41
<212> TYPE: DNA
<213> ORGANISM: Human immunodeficiency virus type 1

<400> SEQUENCE: 27
tagcacccga gtgctcccaa tcccccttt tctgttaaaa t                   41

<210> SEQ ID NO 28
<211> LENGTH: 42
<212> TYPE: DNA
<213> ORGANISM: Human immunodeficiency virus type 1

<400> SEQUENCE: 28
tagcacccga gtgctcccca atccccccctt ttctgttaaa at                42

<210> SEQ ID NO 29
<211> LENGTH: 40
<212> TYPE: DNA
<213> ORGANISM: Human immunodeficiency virus type 1

<400> SEQUENCE: 29
tagcacccga gtgctccaat cccccctttt ctgttaaaat                    40

<210> SEQ ID NO 30
<211> LENGTH: 39
<212> TYPE: DNA
<213> ORGANISM: Human immunodeficiency virus type 1

<400> SEQUENCE: 30
tagcacccga gtgctcaatc cccccttttc tgttaaaat                     39

<210> SEQ ID NO 31
<211> LENGTH: 39
<212> TYPE: DNA
<213> ORGANISM: Human immunodeficiency virus type 1

<400> SEQUENCE: 31
tagcacccga gtgctcaatc cccccttttc ttttaaaat                     39

<210> SEQ ID NO 32
<211> LENGTH: 36
<212> TYPE: DNA
<213> ORGANISM: Human immunodeficiency virus type 1

<400> SEQUENCE: 32
tagcacccga gtgctcccaa tccccccttt tctttt                        36
```

```
<210> SEQ ID NO 33
<211> LENGTH: 37
<212> TYPE: DNA
<213> ORGANISM: Human immunodeficiency virus type 1

<400> SEQUENCE: 33
tagcacccga gtgctcccaa tccccctttt tctttta                              37

<210> SEQ ID NO 34
<211> LENGTH: 16
<212> TYPE: DNA
<213> ORGANISM: Human immunodeficiency virus type 1

<400> SEQUENCE: 34
ctaaaggaag ctctat                                                     16

<210> SEQ ID NO 35
<211> LENGTH: 14
<212> TYPE: DNA
<213> ORGANISM: Human immunodeficiency virus type 1

<400> SEQUENCE: 35
aacctccaat tccc                                                       14

<210> SEQ ID NO 36
<211> LENGTH: 23
<212> TYPE: DNA
<213> ORGANISM: Human immunodeficiency virus type 1

<400> SEQUENCE: 36
gaatctatga ataaagaatt aaa                                             23

<210> SEQ ID NO 37
<211> LENGTH: 21
<212> TYPE: DNA
<213> ORGANISM: Human immunodeficiency virus type 1

<400> SEQUENCE: 37
tgctattatg tctactattc t                                               21
```